(12) United States Patent
Okumura et al.

(10) Patent No.: US 9,149,546 B2
(45) Date of Patent: Oct. 6, 2015

(54) COMPOUND HAVING AFFINITY FOR AMYLOID

(75) Inventors: Yuki Okumura, Sodegaura (JP); Yoshifumi Maya, Sodegaura (JP); Yoshinari Shoyama, Sodegaura (JP); Takako Onishi, Sodegaura (JP)

(73) Assignee: NIHON MEDI-PHYSICS CO., LTD., Tokyo (JP)

( * ) Notice: Subject to any disclaimer, the term of this patent is extended or adjusted under 35 U.S.C. 154(b) by 0 days.

(21) Appl. No.: 14/118,317

(22) PCT Filed: May 18, 2012

(86) PCT No.: PCT/JP2012/062778
§ 371 (c)(1),
(2), (4) Date: Apr. 30, 2014

(87) PCT Pub. No.: WO2012/161116
PCT Pub. Date: Nov. 29, 2012

(65) Prior Publication Data
US 2014/0228569 A1    Aug. 14, 2014

(30) Foreign Application Priority Data
May 20, 2011   (JP) ................ 2011-114198

(51) Int. Cl.
| C07F 15/00 | (2006.01) |
|---|---|
| C07D 491/02 | (2006.01) |
| C07D 471/02 | (2006.01) |
| C07D 498/02 | (2006.01) |
| C07D 513/02 | (2006.01) |
| C07D 515/02 | (2006.01) |
| A61K 31/44 | (2006.01) |
| A61K 51/00 | (2006.01) |
| A61K 51/04 | (2006.01) |
| C07D 471/04 | (2006.01) |
| C07F 7/22 | (2006.01) |

(52) U.S. Cl.
CPC ......... *A61K 51/0455* (2013.01); *A61K 51/0453* (2013.01); *C07D 471/04* (2013.01); *C07F 7/2212* (2013.01)

(58) Field of Classification Search
None
See application file for complete search history.

(56) References Cited

U.S. PATENT DOCUMENTS

| 6,946,116 | B2 | 9/2005 | Kung et al. | |
|---|---|---|---|---|
| 8,022,075 | B2 * | 9/2011 | Bando et al. | 514/259.2 |
| 8,303,935 | B2 | 11/2012 | Tanifuji et al. | |
| 8,399,672 | B2 | 3/2013 | Tanifuji et al. | |
| 2004/0131545 | A1 | 7/2004 | Kung et al. | |
| 2009/0162283 | A1 * | 6/2009 | Bando et al. | 424/1.89 |
| 2009/0252679 | A1 | 10/2009 | Tanifuji et al. | |
| 2010/0249408 | A1 | 9/2010 | Tanifuji et al. | |
| 2010/0249418 | A1 | 9/2010 | Tanifuji et al. | |
| 2010/0249419 | A1 | 9/2010 | Tanifuji et al. | |
| 2010/0267952 | A1 | 10/2010 | Tanifuji et al. | |
| 2010/0292479 | A1 | 11/2010 | Tanifuji et al. | |

FOREIGN PATENT DOCUMENTS

| EP | 1956013 A1 | 8/2008 |
|---|---|---|
| EP | 2019103 A1 | 1/2009 |
| EP | 2213671 A1 | 8/2010 |
| EP | 2213672 A1 | 8/2010 |
| EP | 2216050 A1 | 8/2010 |
| EP | 2216051 A1 | 8/2010 |
| EP | 2218463 A1 | 8/2010 |
| JP | 2002-523383 A | 7/2002 |
| JP | 2004-506723 A | 3/2004 |
| JP | 2005-504055 A | 2/2005 |
| JP | 2005-512945 A | 5/2005 |
| WO | 02/085903 A2 | 10/2002 |
| WO | 2007/063946 A1 | 6/2007 |
| WO | 2007/135890 A1 | 11/2007 |
| WO | 2009/054496 A1 | 4/2009 |
| WO | 2009/054497 A1 | 4/2009 |
| WO | 2009/057575 A1 | 5/2009 |
| WO | 2009/057576 A1 | 5/2009 |
| WO | 2009/057578 A1 | 5/2009 |

(Continued)

OTHER PUBLICATIONS

Matsushima, CAS Registry No. 1254328-87-4, entered Nov. 29, 2010, CAPLUS database, p. 3.*
International Search Report dated Aug. 21, 2012, issued in International Application PCT/JP2012/062778.
Agdeppa et al., "2-Dialkylamino-6-Acylmalononitrile Substituted Naphthalenes (DDNP Analogs): Novel Diagnostic and Therapeutic Tools in Alzheimer's Disease", Molecular Imaging and Biology, vol. 5, No. 6, 2003, pp. 404-417.
Furumoto et al., "[11c]bf-227: A New C-Labeled 2-Ethenylbenzoxazole Derivative for Amyloid-B Plaques Imaging", Radiochemistry: European Journal of Nuclear Medicine and Molecular Imaging, vol. 32, Sup. 1, 2005, PET, P759.
Hardy et al., "Alzheimer's Disease: The Amyloid Cascade Hypothesis", Perspective, Science, vol. 256, Apr. 10, 1992, pp. 184-185.

(Continued)

Primary Examiner — Rita Desai
Assistant Examiner — Ben S Michelson
(74) Attorney, Agent, or Firm — Fitch, Even, Tabin & Flannery LLP

(57) ABSTRACT

A compound that is effective as a diagnostic imaging probe that targets amyloid including is represented by the following formula (1), or salt thereof:

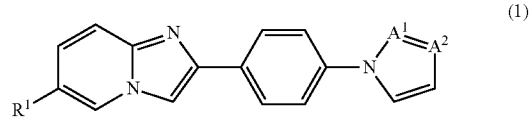

(1)

wherein $R^1$ is a radioactive halogen substituent, $A^1$ and $A^2$ independently represent CH or N. A diagnostic agent for Alzheimer's disease includes the compound represented by the above formula or a salt thereof. The above compound and the above diagnostic agent for Alzheimer's disease transfer into brain after administration, and indicate good accumulation on amyloid deposited in the brain.

5 Claims, 3 Drawing Sheets

(56) References Cited

FOREIGN PATENT DOCUMENTS

| WO | 2010/128595 A1 | 11/2010 |
| WO | WO 2010/128595 A1 * | 11/2010 |

OTHER PUBLICATIONS

Klunk et al., "Imaging Brain Amyloid in Alzheimer's Disease with Pittsburgh Compound-B", Annals of Neurology, vol. 55, No. 3, Mar. 2004, pp. 306-319.

Kung et al., "Novel Stilbenes as Probes for Amyloid Plaques", J. Am. Chem. Society, vol. 123, No. 50, 2001, pp. 12740-12741.

McKhan et al., "Clinical diagnosis of Alzheimer's disease: Report of the NINCDS-ADRDA Work Group* under the auspices of Department of Heath and Human Services Task Force on Alzheimer's Disease", Neurology, vol. 34, Jul. 1984, pp. 939-944.

Ono et al., "C-labeled stilbene derivatives as AB-aggregate-specific PET imaging agents for Alzheimer's disease", Elsevier, Nuclear Medicine and Biology, vol. 30, 2003, pp. 565-571.

Verhoeff et al., "In-Vivo Imaging of Alzheimer Disease B-Amyloid With [11C]SB-13 PET", Am. J. Geriatr Psychiatry, 12:6, Nov.-Dec. 2004, pp. 584-595.

Zhuang et al., "Radioiodinated Styrylbenzenes and Thioflavins as Probes for Amyloid Aggregates", J. Med. Chem., vol. 44, 2001, pp. 1905-1914.

Zhuang et al., "IBOX(2-(4'-dimethylaminophenyl)-6-iodobenzoxazole): a ligand for imaging amyloid plaques in the brain", Elsevier, Nuclear Medicine and Biology, vol. 28, 2001, pp. 887-894.

Zhuang et al., "Structure-Activity Relationship of Imidazo[1,2-a]pyridines as Ligands for Detecting B-Amyloid Plaques in the Brain", J. Med. Chem., vol. 46, 2003, pp. 237-243.

Newberg et al., "Safety, Biodistribution, and Dosimetry of 123I-IMPY: A Novel Amyloid Plaque-Imaging Agent for the Diagnosis of Alzheimer's Disease", The Journal of Nuclear Medicine, vol. 47, No. 5, May 2006, pp. 748-754.

Arai et al., "[11C]-BF-227 and PET to Visualize Amyloid in Alzheimer's Disease Patents", Alzheimer's & Dementia: The Journal of the Alzheimer's Association, 2006, 2, Sup. 1, p. S312.

Clark et al., "Imaging Amyloid With I123 IMPY SPECT", Alzheimer's & Dementia: The Journal of the Alzheimer's Association, 2006, 2, Sup. 1, p. S342.

Notification of Transmittal of Translation of the International Preliminary Report on Patentability dated Nov. 28, 2013 together with the Translation of Written Opinion of the International Searching Authority dated Aug. 21, 2012.

European Search Report dated Nov. 10, 2014, issued against European Patent Application 12789191.9.

Office Action dated Dec. 2, 2014, issued in Chinese Patent Application No. 201280023320.8.

* cited by examiner

COMPOUND HAVING AFFINITY FOR AMYLOID

CROSS-REFERENCE TO RELATED APPLICATIONS

This Application is a U.S. National Stage Application filed under 35 U.S.C. §371 of International Application PCT/JP2012/062778, filed May 18, 2012, designating the United States, which claims priority from Japanese Patent Application 2011-114198, filed May 20, 2011, the complete disclosures of which are hereby incorporated herein by reference in their entirety for all purposes.

TECHNICAL FIELD

The present invention relates to a compound for use in diagnosis of cerebral degenerative disease. More specifically, the invention relates to a compound useful for amyloid detection at lesion sites in diagnosis of Alzheimer's disease and other diseases with amyloid accumulation.

BACKGROUND ART

Diseases with the onset of deposition of a fibrous protein called amyloid in various organs or tissues in bodies are generally referred to as amyloidosis. A feature common to amyloidosis is that the fibrous protein called amyloid which is enriched with the β-sheet structure is deposited at various organs systemically or at sites topically so that functional abnormalities are triggered in the organs or tissues.

Alzheimer's disease (hereinafter referred to as AD), which is a typical amyloidosis disease, is known as a disease causing dementia. This disease is lethal with progressive deposition of amyloid in brain, and thus is said to be a disease that causes concern in society compared with other amyloidosis diseases. In recent years, the number of AD patients is rapidly increasing in developed countries with aging societies, thereby causing a social problem.

From the pathohistological viewpoint, AD is characterized by three pathological findings in brain, namely development of senile plaques, formation of neurofibrillary tangles, and extensive neuronal loss. The senile plaque has a structure mainly composed of amyloid, and is said to appear at the earliest stage of AD onset and thus is pathologically found in brain 10 or more years before appearance of clinical symptoms.

AD is diagnosed by carrying out various evaluations of cognitive functions (for example, Hasegawa scale, ADAS-JCog and MMSE) in auxiliary combination with imaging diagnosis such as CT and MRI. However, the method based on such evaluations of cognitive functions is low in diagnostic sensitivity at the early stage of the onset, and is furthermore problematic in that diagnostic results are susceptible to inborn cognitive functions of individuals. At present, it is practically impossible to establish a definite diagnosis of AD while an AD patient is still alive, because the definite diagnosis requires a biopsy of a lesion (Non-Patent Document 1).

Meanwhile, a report tells that amyloid constituting senile plaques is an aggregate of amyloid β protein (hereinafter referred to as Aβ). Also, numerous reports tell that the Aβ aggregate forms a β-sheet structure that causes nerve cell toxicity. Based on these findings, the so-called "Amyloid Cascade Hypothesis" is proposed, which suggests that cerebral deposition of Aβ triggers the downstream phenomena, namely, formation of neurofibrillary tangles and neuronal loss (Non-Patent Document 2).

Based on these facts, attempts have recently been made to detect AD in vivo using a compound having high affinity with amyloid as a marker.

Many of such probes for imaging diagnoses of cerebral amyloid are hydrophobic low-molecular weight compounds that are high in affinity with amyloid and high in cerebral transferability and are labeled with various radioactive species such as $^{11}C$, $^{18}F$ and $^{123}I$. For example, reports tell $^{11}C$ or radioactive halogen labeled forms of compounds including various thioflavin derivatives such as 6-iodo-2-[4'-(N,N-dimethylamino)phenyl]benzothiazole (hereinafter referred to as TZDM) and 6-hydroxy-2-[4'-(N-methylamino)phenyl]benzothiazole (hereinafter referred to as 6-OH-BTA-1) (Patent Document 1, Non-Patent Document 3); stilbene compounds such as (E)-4-methylamino-4'-hydroxystilbene (hereinafter referred to as SB-13) and (E)-4-dimethylamino-4'-iodostilbene (hereinafter referred to as m-I-SB) (Patent Document 2, Non-Patent Document 4, Non-Patent Document 5); benzoxazole derivatives such as 6-iodo-2-[4'-(N,N-dimethylamino)phenyl]benzoxazole (hereinafter referred to as IBOX) and 6-[2-(fluoro)ethoxy]-2-[2-(2-dimethylaminothiazol-5-yl)ethenyl]benzoxazole (Non-Patent Document 6, Non-Patent Document 7), DDNP derivatives such as 2-(1-{6-[(2-fluoroethyl)(methyl)amino]-2-naphthyl}ethylidene)malononitrile (hereinafter referred to as FDDNP) (Patent Document 4, Non-Patent Document 8); and imidazopyridine derivatives such as 6-iodo-2-[4'-(N,N-dimethylamino)phenyl]imidazo[1,2-a]pyridine (hereinafter referred to as IMPY) (Patent Document 3, Non-Patent Document 9), and radioactive halogen labeled forms of compounds including compounds in which a nitrogen-containing 5-membered aromatic heterocyclic group is attached to an imidazopyridine-phenyl via carbons (Patent Document 5 and Patent Document 6). Further, some of these probes for imaging diagnosis have been studied on human imaging and have been reported to show a significant accumulation of radioactivity in AD patient's brain compared with normal persons (Non-Patent Document 10, Non-Patent Document 11, Non-Patent Document 12, Non-Patent Document 13).

CONVENTIONAL TECHNICAL DOCUMENTS

Patent Documents

[Patent Document 1] JP-T-2004-506723
[Patent Document 2] JP-T-2005-504055
[Patent Document 3] JP-T-2005-512945
[Patent Document 4] JP-T-2002-523383
[Patent Document 5] International Publication No. WO2007/063946 pamphlet
[Patent Document 6] International Publication No. WO2010/128595 pamphlet

Non-Patent Documents

[Non-Patent Document 1] J. A. Hardy & G. A. Higgins, "Alzheimer's Disease: The Amyloid Cascade Hypothesis.", Science, 1992, 256, p. 184-185
[Non-Patent Document 2] G. McKhann et al., "Clinical diagnosis of Alzheimer's disease: Report of the NINCDS-ADRDA Work Group under the auspices of Department of Health and Human Services Task Force on Alzheimer's Disease.", Neurology, 1984, 34, p. 939-944
[Non-Patent Document 3] Z.-P. Zhuang et al., "Radioiodinated Styrylbenzenes and Thioflavins as Probes for Amyloid Aggregates.", J. Med. Chem., 2001, 44, p. 1905-1914

[Non-Patent Document 4] Masahiro Ono et al., "11C-labeled stilbene derivatives as Aβ-aggregate-specific PET imaging agents for Alzheimer's disease.", Nuclear Medicine and Biology, 2003, 30, p. 565-571

[Non-Patent Document 5] H. F. Kung et al., "Novel Stilbenes as Probes for amyloid plaques.", J. American Chemical Society, 2001, 123, p. 12740-12741

[Non-Patent Document 6] Zhi-Ping Zhuang et al., "IBOX(2-(4'-dimethylaminophenyl)-6-iodobensoxazole): a ligand for imaging amyloid plaques in the brain.", Nuclear Medicine and Biology, 2001, 28, p. 887-894

[Non-Patent Document 7] Furumoto Y et al., "[$^{11}$C]BF-227: A New $^{11}$C-Labeled 2-Ethenylbenzoxazole Derivative for Amyloid-β Plaques Imaging.", European Journal of Nuclear Medicine and Molecular Imaging, 2005, 32, Sup. 1, P759

[Non-Patent Document 8] Eric D. Agdeppa et al., "2-Dialkylamino-6-Acylmalononitrile Substituted Naphthalenes (DDNP Analogs): Novel Diagnostic and Therapeutic Tools in Alzheimer's Disease.", Molecular Imaging and Biology, 2003, 5, p. 404-417

[Non-Patent Document 9] Zhi-Ping Zhuang et al., "Structure-Activity Relationship of Imidazo[1,2-a]pyridines as Ligands for Detecting β-Amyloid Plaques in the Brain.", J. Med. Chem., 2003, 46, p. 237-243

[Non-Patent Document 10] W. E. Klunk et al., "Imaging brain amyloid in Alzheimer's disease with Pittsburgh Compound-B.", Ann. Neurol., 2004, 55, p. 306-319

[Non-Patent Document 11] Nicolaas P. L. G. Verhoeff et al., "In-Vivo Imaging of Alzheimer Disease β-Amyloid With [11C]SB-13 PET.", American Journal of Geriatric Psychiatry, 2004, 12, p. 584-595

[Non-Patent Document 12] Hiroyuki Arai et al., "[11C]-BF-227 AND PET to Visualize Amyloid in Alzheimer's Disease Patients", Alzheimer's & Dementia: The Journal of the Alzheimer's Association, 2006, 2, Sup. 1, S312

[Non-Patent Document 13] Christopher M. Clark et al., "Imaging Amyloid with I123 IMPY SPECT", Alzheimer's & Dementia: The Journal of the Alzheimer's Association, 2006, 2, Sup. 1, S342

DISCLOSURE OF THE INVENTION

Problems to be Solved by the Invention

As described above, various compounds are disclosed as probes for imaging diagnosis for amyloid, and researched for clinical application. However, there has been no compound which is confirmed to have a clinically tolerable property. In addition, considering a broad range of clinical application, a compound having a sufficient diagnosing property in case of being labeled not only by PET isotope, but also SPECT isotope is desired.

The present invention has been made under the above-mentioned circumstances, and aims at providing a compound that is effective as a probe targeting amyloid for imaging diagnosis and a diagnostic agent for Alzheimer's disease comprising the compound.

Means for Solving the Problems

As a result of repeated studies, the inventors have found that an amyloidosis diagnostic agent having a sufficient diagnostic property can be obtained by using a compound in which a 5-membered nitrogen-containing heterocycle is attached to a carbon at 4'-position of the phenyl group of an imidazopyridine-phenyl skeleton via a nitrogen atom of the nitrogen-containing heterocycle, and thus have completed the present invention.

According to one aspect of the present invention, a compound represented by the following formula (1):

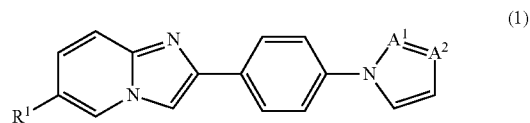

or a salt thereof, and a diagnostic agent for Alzheimer's disease comprising a compound represented by the above formula (1) or a salt thereof are provided.

In the formula (1), $R^1$ is a radioactive halogen substituent. As $R^1$, can be used various radioactive halogens, preferably a radioactive halogen selected from the group consisting of $^{18}$F, $^{76}$Br, $^{123}$I, $^{124}$I, $^{125}$I and $^{131}$I, and more preferably $^{18}$F or $^{123}$I.

$A^1$ and $A^2$ independently represent CH or N.

Therefore, according to a preferable embodiment of the present invention, a compound represented by the following formula (3), (4) or (5):

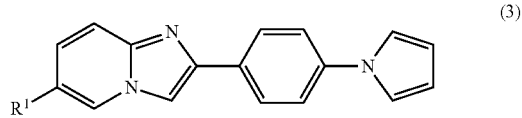

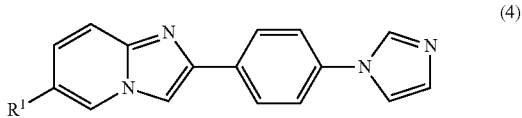

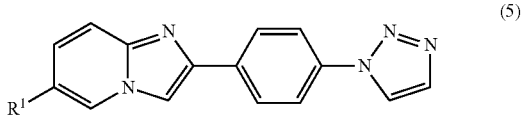

or a salt thereof, and a diagnostic agent for Alzheimer's disease comprising a compound represented by the above formula (3), (4) or (5) or a salt thereof are provided.

According to another aspect of the present invention, a compound represented by the following formula (2):

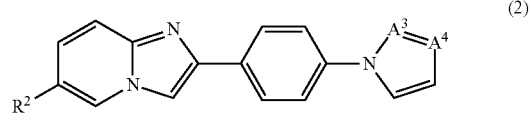

or a salt thereof is provided.

In the formula (2), $R^2$ is a group selected from the group consisting of a non-radioactive halogen substituent, nitro group, trialkylammonium group having alkyl chains with 1 to 4 carbon atoms, trialkylstannyl substituent having alkyl chains with 1 to 4 carbon atoms or triphenylstannyl group. $A^3$ and $A^4$ independently represent CH or N.

The compound represented by the formula (2) can be suitably used as a labeling precursor for the compound of the above mentioned formula (1).

As a non-radioactive halogen substituent, a halogen capable of being a target of nucleophilic substitution reactions using a radioactive fluorine or a halogen capable of being a target of isotope exchange reactions with a radioactive iodine can be used, and preferably chlorine, iodine or bromine can be used. As a trialkylstannyl substituent, various substituents can be used, and trimethylstannyl substituent and tributylstannyl substituent are preferably used.

Therefore, according to a preferable embodiment of the present invention, a compound represented by the following formula (6), (7) or (8) is provided:

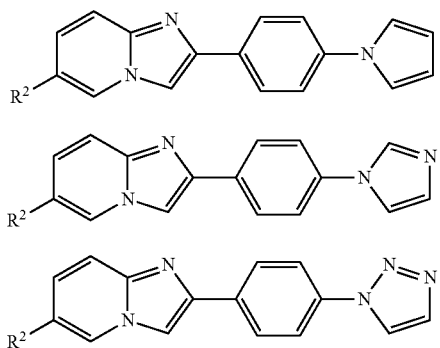

Effects of the Invention

According to the present invention, a novel compound having affinity with amyolid and a diagnostic agent for Alzheimer's disease have become available, which have an excellent capability of imaging amyloid in living bodies.

BEST MODE FOR CARRYING OUT THE INVENTION (A Method for Synthesis of a Precursor Compound for a Radioactive Halogen-labeled Compound)

Hereinafter, a method for synthesis of a precursor compound for a radioactive halogen-labeled compound according to an embodiment of the present invention is described, taking the case of 2-[4-(1H-1,2,3,-triazole-1-yl)phenyl]-6-tributylstannylimidazo[1,2-a]pyridine as an example. The present compound is a compound which is suitably used as a precursor compound for a radioactive iodine-labeled compound according to the present invention.

Figure 1:
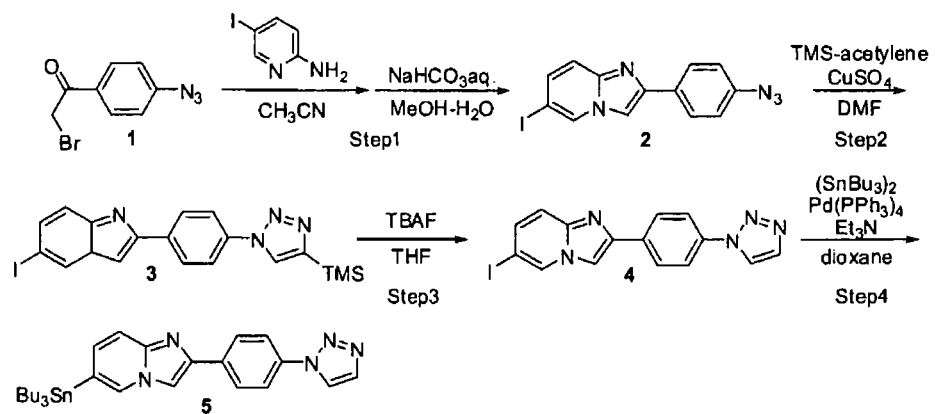
FIG. 1 is a scheme of synthesis of 2-[4-(1H-1,2,3,-triazole-1-yl)phenyl]-6-tributylstannylimidazo[1,2-a]pyridine.

FIG. 1 shows a scheme of synthesis of 2-[4-(1H-1,2,3,-triazole-1-yl)phenyl]-6-tributylstannylimidazo[1,2-a]pyridine. For the synthesis of 2-[4-(1H-1,2,3,-triazole-1-yl)phenyl]-6-tributylstannylimidazo[1,2-a]pyridine, 4-azidophenacylbromide is first allowed to react with 2-amino-5-iodopyridine to prepare 2-(4-azidophenyl)-6-iodoimidazo[1,2-a]pyridine (FIG. 1, step 1). In this instance, the reaction can be conducted in accordance with ordinary methods, for example, the method described in a literature, Zhi-Ping Zhuang et al., J. Med. Chem, 2003, 46, p. 237-243.

Then, 6-iodo-2-(4-azidophenyl)imidazo[1,2-a]pyridine as prepared above is allowed to react with trimethylsilyl acetylene to obtain 6-iodo-2-[4-(4-trimethylsilyl-1H-1,2,3,-triazole-1-yl)phenyl]imidazo[1,2-a]pyridine (FIG. 1, step 2) in accordance with known methods (for example, the method described in a literature, James T. Fletcher et al., Tetrahedron Lett, 2008, 49, p. 7030-7032), and then trimethylsilyl group is removed (FIG. 1, step 3), to obtain 6-iodo-2-[4-(1H-1,2,3,-triazole-1-yl)phenyl]imidazo[1,2-a]pyridine.

Next, the obtained 6-iodo-2-[4-(1H-1,2,3,-triazole-1-yl) phenyl]imidazo[1,2-a]pyridine is allowed to react with bis (tributyltin) (FIG. 1, step 4) in accordance with known methods (for example, the method described in a literature, Zhi-Ping Zhuang et al., J. Med. Chem, 2003, 46, p. 237-243), and purified to obtain 2-[4-(1H-1,2,3,-triazole-1-yl)phenyl]-6-tributylstannylimidazo[1,2-a]pyridine as the target compound.

When a compound with a substituent at 6-position of the imidazo pyridine ring being a trialkylstannyl substituent other than the tributylstannyl substituent is obtained, various bis(trialkyltin)s that fit purposes can be used instead of bis (tributyltin) in step 4 of FIG. 1. For example, when a compound having a trimethylstannyl substituent as a substituent at the 6-position is synthesized, a reaction similar to the above may be performed using bis(trimethyltin) in step 4 of FIG. 1.

In addition, other precursor compounds according to the present invention can be synthesized by using generally-available raw materials and combining reactions known to the skilled in the art. For example, a compound with an imidazopyridine ring in which the substituent at 6-position is a nitro group can be synthesized by using 2-amino-5-nitropyridine instead of 2-amino-5-iodopyridine in step 1 of FIG. 1 in accordance with known methods. A compound in which both $A^3$ and $A^4$ are CH in the above formula (2) can be synthesized in accordance with the above steps of FIG. 1, except that 4-(1H-pyrrole-1-yl)phenacylbromide is used instead of 4-azidophenacylbromide in step 1 of FIG. 1, and the step 3 of FIG. 1 is omitted. A compound in which $A^3$ is CH and $A^4$ is N in the above formula (2) can be synthesized in accordance with the above steps of FIG. 1, except that 4-(1H-imidazole-1-yl)phenacylbromide is used instead of 4-azidophenacylbromide in step 1 of FIG. 1, and the step 3 of FIG. 1 is omitted.
(A Method for Synthesis of a Radioactive Halogen-labeled Compound)

Next, a method for production of a radioactive halogen-labeled compound according to another aspect of the present invention will be described, taking the case of radioactive iodine-labeled compounds as examples.

The synthesis of radioactive iodine-labeled compounds can be performed by dissolving, in an inert organic solvent, the labeling precursor compound prepared in a manner as described above, adding thereto a [$^{123}$I]sodium iodide solution or the like obtained by known methods, and adding thereto an acid and an oxidizing agent so as to allow a reaction to proceed. As the inert organic solvent in which the labeling precursor compound is dissolved, various solvents having no reactivity with the labeling precursor and [$^{123}$I]sodium iodide or the like can be used, and preferably acetonitrile can be used.

As the acid, various acids can be used, and preferably hydrochloric acid can be used.

The oxidizing agent is not particularly limited as long as it can effect the oxidation of iodine in the reaction solution, and is preferably hydrogen peroxide or peracetic acid. The amount of the oxidizing agent to be added may be an amount sufficient to oxidize iodine in the reaction solution.

A compound labeled with a radioactive halogen other than iodine can be synthesized by labeling a labeling precursor that fits a purpose of synthesis with a radioactive halogen that fits the purpose. For example, in order to synthesize [$^{19}$F]-6-fluoro-2-[4-(1H-1,2,3,-triazole-1-yl)phenyl]imidazo[1,2-a]pyridine, the labeling precursor 6-nitro-2-[4-(1H-1,2,3,-triazole-1-yl)phenyl]imidazo[1,2-a]pyridine can be reacted with [$^{18}$F]fluoride ion in the presence of a phase transfer catalyst and potassium carbonate.

(Methods for Preparing and Using a Diagnostic Agent in Accordance with the Present Invention)

The diagnostic agent according to the present invention can be prepared as a solution which comprises the present radioactive halogen-labeled compound blended in water, a physiological saline solution or a Ringer's solution optionally adjusted to an appropriate pH, like other commonly-known radioactive diagnostic agents. In this instance, concentration of the present compound should be adjusted to not more than the concentration at which stability of the present compound is ensured. Dosage of the present compound is not specifically limited as long as it is sufficient to obtain an image of distribution of an administered agent. For example, when $^{123}$I-labeled compounds or $^{18}$F-labeled compounds are used, about 50 to 600 MBq per adult body of 60 kg weight can be administered intravenously or locally. Distribution of administered agents can be imaged by known methods. For example, $^{123}$I-labeled compounds can be imaged by a SPECT apparatus while $^{18}$F-labeled compounds can be imaged by a PET apparatus.

EXAMPLE

Hereinafter, the present invention is explained below in more detail by describing Examples, Comparative Examples and Reference Examples. However, these Examples never limit the scope of the present invention.

In the following Examples, the names of the individual compounds used in the experiment are defined as shown in Table 1.

TABLE 1

Names of compounds used for evaluation in Examples

| Compound name | Common name |
|---|---|
| Compound 1 | [$^{123}$I]-6-iodo-2-[4-(1H-1,2,3,-triazole-1-yl)phenyl]imidazo[1,2-a]pyridine |
| Compound 2 | [$^{123}$I]-6-iodo-2-[4-(1H-pyrrole-1-yl)phenyl]imidazo[1,2-a]pyridine |
| Compound 3 | 6-iodo-2-[4-(1H-1,2,3,-triazole-1-yl)phenyl]imidazo[1,2-a]pyridine (non-radioactive iodine labeled compound of Compound 1) |

Example 1

Synthesis of 2-[4-(1H-1,2,3,-triazole-1-yl)phenyl]-6-tributylstannylimidazo[1,2-a]pyridine (FIG. 1)

218 mg (corresponding to 0.909 mmol) of 4-azidophenacylbromide and 200 mg (corresponding to 0.909 mmol) of 2-amino-5-iodopyridine were dissolved in 1.0 mL of acetonitrile. The resulting solution was heated in an oil bath at 80° C. for 3 hours. After the completion of the reaction, the reaction solution was cooled down to room temperature, and precipitates were filtered. Then, the precipitates were washed with acetonitrile and dried under reduced pressure. The resulting crude crystals were suspended in a mixed solution of 3 mL of water and 3 mL of methanol. Then, about 4 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 214 mg (corresponding to 0.593 mmol) of 2-(4-azidophenyl)-6-iodoimidazo[1,2-a]pyridine (FIG. 1, step 1).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.89 (s, 1H), 8.31 (s, 1H), 7.99 (d, J=8.7 Hz, 2H), 7.42 (s, 1H), 7.42 (s, 1H), 7.19 (d, J=8.7 Hz, 2H).

Figure 2:
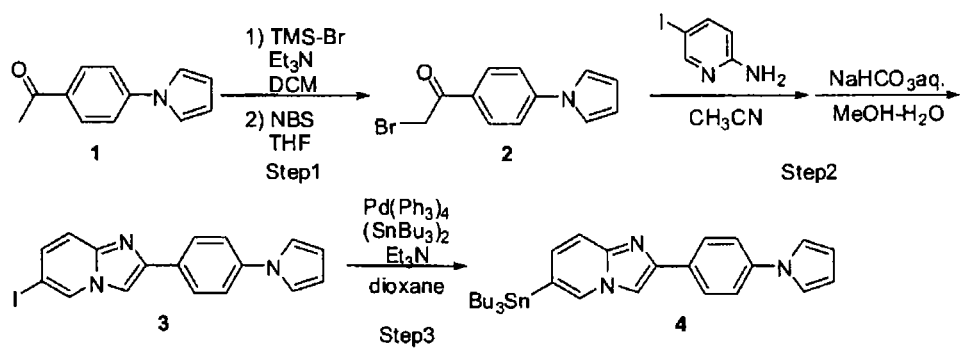
FIG. 2 is a scheme of synthesis of 2-[4-(1H-pyrrole-1-yl)phenyl]-6-tributylstannylimidazo[1,2-a]pyridine.

214 mg (corresponding to 0.593 mmol) of the resulting 2-(4-azidophenyl)-6-iodoimidazo[1,2-a]pyridine was dissolved in 3.0 mL of dimethylformamide, and 0.164 mL (corresponding to 1.18 mmol) of trimethylsilylacetylene was added thereto. Then, 29.6 mg (corresponding to 0.118 mmol) of copper (II) sulfate pentahydrate was added thereto, and heated under stirring at 80° C. for 3 hours. After the completion of the reaction, the reaction solution was cooled down to room temperature, and 5 mL of water was added thereto. The deposited solid matter was filtered, and sufficiently washed with water. The resulting solid matter was dried under reduced pressure, to obtain 137 mg of crude crystals of 6-iodo-2-[4-(4-trimethylsilyl-1H-1,2,3,-triazole-1-yl)phenyl]imidazo[1,2-a]pyridine (FIG. 2, step 2).

137 mg of crude crystals of the resulting 6-iodo-2-[4-(4-trimethylsilyl-1H-1,2,3,-triazole-1-yl)phenyl]imidazo[1,2-a]pyridine was suspended in 3.0 mL of tetrahydrofuran, and 0.3 mL of a 1.0 mol/L solution in tetrahydrofuran of tetrabutylammonium fluoride was added thereto. The resulting solution was stirred under heat and reflux for 4 hours. Then, the reaction solution was cooled down to room temperature, and precipitates were filtered. The precipitates were washed with tetrahydrofuran and diethyl ether, and dried under reduced pressure. The resulting crude crystals were suspended in a mixed solution of 2.0 mL of methanol. Then, about 3 mL of a saturated sodium hydrogencarbonate solution was added thereto, and the mixture was sonicated for 15 minutes using an ultrasonic washing machine. Precipitates were filtered and recovered from the resulting mixture, sufficiently washed with water, and dried under reduced pressure, to obtain 97.4 mg (corresponding to 0.252 mmol) of 6-iodo-2-[4-(1H,1,2,3,-triazole-1-yl)phenyl]imidazo[1,2-a]pyridine (4) (FIG. 1, step 3).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.92 (s, 1H), 8.84 (d, J=0.9 Hz, 1H), 8.41 (s, 1H), 8.15 (d, J=8.7 Hz, 2H), 7.98 (d, J=8.7 Hz, 2H), 7.96 (d, J=0.9 Hz, 1H), 7.45 (s, 1H).

50 mg (corresponding to 0.129 mmol) of 6-iodo-2-[4-(1H-1,2,3,-triazole-1-yl)phenyl]imidazo[1,2-a]pyridine was dissolved in 2.0 mL of dioxane, and 0.5 mL of triethylamine was added thereto. Then, 0.129 mL (corresponding to 0.258 mmol) of bis(tributyltin) and 14.9 mg (a catalytic amount) of tetrakis-triphenylphosphine palladium were added thereto. After the reaction mixture was stirred at 100° C. for 16 hours, the solvent was distilled off under reduced pressure. The residue was purified by flash silica gel column chromatography (elution solvent: hexane/ethyl acetate=2/1), to obtain 43 mg (corresponding to 0.078 mmol) of 2-[4-(1H-1,2,3,-triazole-1-yl)phenyl]-6-tributylstannylimidazo[1,2-a]pyridine as a target compound (FIG. 1, step 4).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.12 (d, J=8.7 Hz, 2H), 8.04 (d, J=1.2 Hz, 1H), 8.01 (s, 1H), 7.90 (s, 1H), 7.87 (d, J=1.2 Hz, 1H), 7.82 (d, J=8.7 Hz, 2H), 7.61 (d, J=8.7 Hz, 1H), 7.20 (d, J=8.7 Hz, 1H), 1.64-1.49 (m, 6H), 1.36 (tt, J=7.3, 7.3 Hz, 6H), 1.20-1.06 (m, 6H), 0.91 (t, J=7.3 Hz, 9H).

Example 2

Synthesis of [$^{123}$I]-6-iodo-2-[4-(1H-1,2,3,-triazole-1-yl)phenyl]imidazo[1,2-a]pyridine (Compound 1)

To 90 μL of a solution (concentration: 1 mg/mL) in acetonitrile of 2-[4-(1H-1,2,3,-triazole-1-yl)phenyl]-6-tributylstannylimidazo[1,2-a]pyridine synthesized in Example 1, 170 μL of 1 mol/L hydrochloric acid, 60 μL of [$^{123}$I]sodium iodide of 674 MBq and 10 μL of 30% (w/v) hydrogen peroxide were added. After the mixed solution was left to stand at 40° C. for 10 minutes, it was subjected to HPLC under the following conditions, to obtain a fraction of [$^{123}$I]-6-iodo-2-[4-(1H-1,2,3,-triazole-1-yl)phenyl]imidazo[1,2-a]pyridine.

HPLC Conditions:
Column: YMC PackPro C8 (trade name; manufactured by YMC; size: 4.6×150 mm)
Mobile phase: 0.1% trifluoroacetic acid/acetonitrile=20/80 to 0/100 (20 minutes)
Flow rate: 1.0 mL/min.
Detector: Ultraviolet visible absorptiometer (Detection wavelength: 260 nm) and radioactivity counter (manufactured by raytest: type STEFFI)

10 mL of water was added to the fraction. The resulting solution was passed through Sep-Pak C18 column (trade name: Sep-Pak (registered trademark) Light C18 Cartridges manufactured by Waters; the packed amount of the packing agent: 130 mg) so that the column adsorbed and collected [$^{123}$I]-6-iodo-2-[4-(1H-1,2,3,-triazole-1-yl)phenyl]imidazo[1,2-a]pyridine. The column was rinsed with 1 mL of water, and then 1 mL of diethyl ether was passed therethrough, to elute [$^{123}$I]-6-iodo-2-[4-(1H-1,2,3,-triazole-1-yl)phenyl]imidazo[1,2-a]pyridine. The obtained radioactivity was 134.5 MBq at the end of synthesis. Further, TLC analysis was conducted under the following conditions, and as a result, the radiochemical purity of the compound was 99.5%.

TLC Analysis Conditions:
TLC plate: TLC plate: Silica Gel 60 $F_{254}$ (trade name; manufactured by Merck & Co., Inc.)
Mobile phase: Chloroform/methanol/diethylamine=100/1/2
Detector: Rita Star (trade name; manufactured by raytest)

Example 3

Synthesis of 2-[4-(1H-pyrrole-1-yl)phenyl]-6-tributylstannylimidazo[1,2-a]pyridine 110 mg (corresponding to 0.594 mmol) of 4-(1H-pyrrole-1-yl)acetophenone was dissolved in 3 mL of dichloromethane and 248 μL of triethylamine, and then 154 μL (corresponding to 1.19 mmol) of bromotrimethylsilane was dropped thereto under ice cooling. The resulting solution was stirred at room temperature overnight under argon atmosphere. Then, the reaction solution was washed with water and a saturated saline solution, and dried over magnesium sulfate. The residue resulted from distillation of the solvent was dissolved in 3.0 mL of tetrahydrofurane, 106 mg (corresponding to 0.594 mmol) of N-bromosuccinimide was added thereto, and the reaction mixture was stirred at room temperature for 30 minutes. After the completion of the reaction, the solvent was distilled under reduced pressure. The residue was purified by flash silica gel column chromatography (elution solvent:hexane/ethyl acetate=7/1), to obtain 120 mg (corresponding to 0.454 mmol) of 4-(1H-pyrrole-1-yl)phenacylbromide (FIG. 2, step 1).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.07 (d, J=8.5 Hz, 2H), 7.70 (d, J=8.5 Hz, 2H), 7.19-7.18 (m, 2H), 6.41-6.40 (m, 1H), 4.44 (s, 2H).

120 mg (corresponding to 0.454 mmol) of 4-(1H-pyrrole-1-yl)phenacylbromide and 99.9 mg (corresponding to 0.454 mmol) of 2-amino-5-iodopyridine were dissolved in 2.0 mL of acetonitrile. The resulting solution was heated under reflux for 2 hours. After the completion of the reaction, the reaction solution was cooled down to room temperature, and precipitates were filtered. The precipitates were washed with acetonitrile and dried under reduced pressure. The resulting crude crystals were suspended in a mixed solution of 10 mL of water and 10 mL of methanol. Then, about 20 mL of a saturated sodium hydrogencarbonate solution was added thereto, and the mixture was sonicated for 20 minutes using an ultrasonic washing machine. Precipitates were filtered and recovered from the resulting mixture, sufficiently washed with water, and dried under reduced pressure, to obtain 120 mg (corresponding to 0.312 mmol) of 6-iodo-2-[4-(1H-pyrrole-1-yl)phenyl]imidazo[1,2-a]pyridine (FIG. 2, step 2).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.90 (s, 1H), 8.34 (s, 1H), 8.02 (d, J=8.7 Hz, 2H), 7.65 (d, J=8.7 Hz, 2H), 7.45-7.41 (m, 3H), 6.19 (brs, 1H).

50 mg (corresponding to 0.129 mmol) of 6-iodo-2-[4-(1H-pyrrole-1-yl)phenyl]imidazo[1,2-a]pyridine was dissolved in 2.0 mL of dioxane, and 0.5 mL of triethylamine was added thereto. Then, 0.130 mL (corresponding to 0.258 mmol) of bis(tributyltin) and 15.0 mg (a catalytic amount) of tetrakistriphenylphosphine palladium were added thereto. After the reaction mixture was stirred at 100° C. for 16 hours, the solvent was distilled off under reduced pressure. The residue was purified by flash silica gel column chromatography (elution solvent: hexane/ethyl acetate=2/1), to obtain 52 mg (corresponding to 0.095 mmol) of 2-[4-(1H-pyrrole-1-yl)phenyl]-6-tributylstannylimidazo[1,2-a]pyridine (FIG. 2, step 3).

NMR apparatus employed: JNM-ECP-500 (manufactured by Japan Electron Optics Laboratory Co., Ltd. (JEOL))

$^1$H-NMR (solvent: chlorofolm-d1; resonance frequency: 500 MHz): δ 8.02-8.00 (m, 3H), 7.83 (s, 1H), 7.60 (d, J=8.7 Hz, 1H), 7.46 (d, J=8.7 Hz, 2H), 7.18-7.14 (m, 3H), 6.37-6.36 (m, 2H), 1.62-1.50 (m, 6H), 1.36 (tt, J=7.3, 7.3 Hz, 6H), 1.19-1.06 (m, 6H), 0.91 (t, J=7.3 Hz, 9H).

Example 4

Synthesis of [$^{123}$I]-6-iodo-2-[4-(1H-pyrrole-1-yl)phenyl]imidazo[1,2-a]pyridine (Compound 2)

To 200 μL of a solution (concentration: 1 mg/mL) in acetonitrile of 2-[4-(1H-pyrrole-1-yl)phenyl]-6-tributylstannylimidazo[1,2-a]pyridine synthesized in Example 3, 200 μL of 1 mol/L sulfuric acid, 12 μL of a 1 mmol/L sodium iodide aqueous solution, 170 μL of [$^{123}$I]sodium iodide of 1243 MBq and 20 μL of 30% (w/v) hydrogen peroxide were added. After the mixed solution was left to stand at 40° C. for 10 minutes, it was subjected to HPLC under the following conditions, to obtain a fraction of [$^{123}$I]-6-iodo-2-[4-(1H-pyrrole-1-yl)phenyl]imidazo[1,2-a]pyridine.

HPLC Conditions:
Column: YMC PackPro C8 (trade name; manufactured by YMC; size: 4.6×150 mm)
Mobile phase: 0.1% trifluoroacetic acid/acetonitrile=20/80 to 0/100 (20 minutes)
Flow rate: 1.0 mL/min.
Detector: Ultraviolet visible absorptiometer (Detection wavelength: 260 nm) and radioactivity counter (manufactured by raytest: type STEFFI)

10 mL of water was added to the fraction. The resulting solution was passed through Sep-Pak C18 column (trade name: Sep-Pak (registered trademark) Light C18 Cartridges manufactured by Waters; the packed amount of the packing agent: 130 mg) so that the column adsorbed and collected [$^{123}$I]-6-iodo-2-[4-(1H-pyrrole-1-yl)phenyl]imidazo[1,2-a]pyridine. The column was rinsed with 1 mL of water, and then 1 mL of diethyl ether was passed therethrough, to elute [$^{123}$I]-6-iodo-2-[4-(1H-pyrrole-1-yl)phenyl]imidazo[1,2-a]pyridine. The obtained radioactivity was 235 MBq at the end of synthesis. Further, TLC analysis was conducted under the following conditions, and as a result, the radiochemical purity of the compound was 98.4%.

TLC Analysis Conditions:
TLC plate: TLC plate: Silica Gel 60 F$_{254}$ (trade name; manufactured by Merck & Co., Inc.)
Mobile phase: Chloroform/methanol/diethylamine=100/1/2
Detector: Rita Star (trade name; manufactured by raytest)

Reference Example 1

Synthesis of [$^{123}$I]-IMPY

[$^{123}$I]-IMPY was synthesized in accordance with the following steps for use in Comparative Examples for evaluation on measurement of log P$_{octanol}$ and accumulation in brain.

In accordance with the method described in a literature (Zhi-Ping Zhuang et al., J. Med. Chem, 2003, 46, p. 237-243), 2-[4'-(N,N-dimethylamino)phenyl]-6-tributylstannylimidazo[1,2-a]pyridine was synthesized, and dissolved in acetonitrile (concentration: 1 mg/mL). To 50 μL of the resulting solution, 50 μL of 2 mol/L hydrochloric acid, 80 μL of [$^{123}$I] sodium iodide of 1075 MBq, 23 μL of a 1 mmol/L sodium iodide solution and 15 μL of 30% (w/v) hydrogen peroxide were added. After the mixed solution was left to stand at 40° C. for 10 minutes, the solution was subjected to HPLC under the same conditions as in Example 2, to obtain a fraction of [$^{123}$I]-IMPY.

10 ml of water was added to the fraction. The resulting solution was passed through Sep-Pak C18 column (trade name: Sep-Pak (registered trademark) Light C18 Cartridges manufactured by Waters; the packed amount of the packing agent: 130 mg), so that the column adsorbed and collected [$^{123}$]-IMPY. The column was rinsed with 1 mL of water, and then 1 mL of diethyl ether was passed therethrough, to elute [$^{123}$I]-IMPY. The obtained radioactivity was 170 MBq at the end of synthesis. Further, TLC analysis was conducted under the same conditions as described in Example 2, and as a result, the radiochemical purity of the compound was 98.5%.

Example 5

Measurement of Partition Coefficient Based on the Octanol Extraction Method

Partition coefficients based on the octanol extraction method (hereinafter referred to as log P$_{octanol}$) were measured, which are generally known as an indicator of permeability of compounds through the blood-brain barrier (hereinafter referred to as BBB).

Compound 1 and Compound 2 were adjusted to about 1 MBq/mL using a water saturated 1-octanol solution, and 30 μL thereof was added to an equilibrated vessel. Water saturated 1-octanol and 1-octanol saturated water were added to the equilibrated vessel each in an amount of 200 μL, 400 μL or 800 μL. The equilibrated vessel was subjected to stirring, and then was shaken for 5 minutes (20 to 25±2° C., 20 rpm). After the respective mixtures were centrifuged (23° C., 3000 g×60 min.) with a centrifuge (type: T2-MC, manufactured by BECKMAN), 50 μL each of water saturated 1-octanol and 1-octanol saturated water was obtained, and subjected to measurement of radioactivity with an Autowell Gamma system (Type: ARC-7001, manufactured by Aloka). Using the obtained count, log P$_{octanol}$ was calculated in accordance with the following equation (1).

$$\log P_{octanol} = \log_{10}\left(\frac{\text{Radioactivity count of octanol layer}}{\text{Radioactivity count of water layer}}\right) \quad (1)$$

The results are shown in Table 2. log P$_{octanol}$ values of Compound 1 and Compound 2 were 1.98 and 2.45, respectively. It is known that an optimum log P$_{octanol}$ value of compounds regarding BBB permeability is between 1 and 3 (Douglas D. Dischino et al., J. Nucl. Med., (1983), 24, p. 1030-1038). From the above results, it is implied that Compound 1 and Compound 2 have a BBB permeability.

TABLE 2

| logP$_{octanol}$ value of the present compound | |
|---|---|
| Compound | logP$_{octanol}$ value |
| Compound 1 | 1.98 |
| Compound 2 | 2.45 |

Example 6

Calculation of Dissociation Constant (Hereinafter, Referred to as K$_d$) and Maximum Binding Amount (Hereinafter, Referred to as B$_{max}$) Resulting from Binding Assay Using Brain Tissue of Patients of Alzheimer's Disease (Hereinafter, Referred to as AD)

The assay was conducted using a brain gray matter homogenate of AD patients, which was prepared from a brain tissue (Frontal lobe) of AD patients commercially available from Analytical Biological Services Inc. (United States).

Method
A mixed solution of Compound 1 (about 35 kBq/100 μL) and Compound 3 (62.5 nmol/L) was diluted with a 0.1% bovin serum albumin (hereinafter referred to as BSA)-containing 5 mmol/L phosphate buffer saline solution, and prepared to have a concentration of 0.2 nmol/L to 25 nmol/L in the reaction solution. To each well of a 96-well microplate, 100 μL of a 0.1% BSA-containing 5 mmol/L phosphate buffer saline solution and 100 μL of the prepared mixed solution of Compound 1 and Compound 3 were added. Then, 50 μL of a 0.5 μg/μL brain gray matter homogenate of AD patients was added thereto to initiate the reaction. After the reaction solution was shaken for 3 hours (22° C., 400 rpm), a glass fiber filter (Multiscreen HTS FB, manufactured by Millipore) was used to filter the reaction mixture. The filter after filtration was washed with a 0.1% BSA-containing 5 mmol/L phosphate buffer saline solution (200 μL×3 times), and then radioactivity remaining in the filter was measured with an Autowell Gamma system (type: ARC-7001, manufactured by Aloka). Non-specific binding was defined as a count when the same procedures were carried out by adding 6-OH-BTA-1 (synthesized in accordance with the method described in a literature (C. A. Mathis et al., J. Med. Chem., (2003), 46, p. 2740)) to have a concentration of 1 μmol/L in the reaction solution. The resulting count was analyzed with GraphPad Prism Ver. 5 (manufactured by GraphPad Software, Inc.), and binding parameter ($K_d$, $B_{max}$) was calculated.

Results

Compound 1 shows $K_d$ to be 4.94 nmol/L, and $B_{max}$ to be 2242 fmol/mg protein. From this result, it was indicated that Compound 1 has a high avidity towards amyloid aggregates in the brain of AD patients.

Example 7

Measurement of Transferability into Brain and Clearance

Using Compound 1 and Compound 2, a time course change of radioactive accumulation in brain of male Wistar rats (8-week old) was measured.

Method

A solution in which Compound 1 and Compound 2 were dissolved in a physiological saline solution containing 50 mmol/L of L-cysteine hydrochloride was prepared respectively, to obtain sample solutions (radioactive concentration of both was 37 MBq/mL). The sample solution was injected under non-anesthesia into the tail vein of male Wistar rats (8-week old) (dosage: 0.2 mL, dosed radioactivity: 7.4 MBq equivalent). The rats were sacrificed by decapitating under non-anesthesia to sample bloods and brains 2, 5, 15, 30 and 60 minutes after the injection. Brains were subjected to measurement of mass of brains and further subjected to measurement of radioactivity (hereinafter referred to as A in this Example) with a single channel analyzer (detector type SP-20 manufactured by OHYO KOKEN KOGYO Co., Ltd.). Further, the radioactivity level of the rest of the whole body including blood was measured in the same manner as above (hereinafter referred to as B in this Example). Using these measurement results, the amount of radioactive accumulation per unit weight of brain (% ID/g) at the respective time points were calculated in accordance with the following formula (2).

Separately, a solution of [$^{123}$I]-IMPY dissolved in a physiological saline solution containing 50 mmol/L of L-cysteine hydrochloride (radioactive concentration: 37 MBq/mL) was prepared. The same procedure as above was carried out to calculate the amount of radioactive accumulation per unit weight of brain (% ID/g) at the respective time points.

Meanwhile, in this Example, three animals were used for the experiment at the respective time points.

$$\% \ ID/g = \frac{A}{B \times \text{brain weight}} \times 100 \qquad (2)$$

Results

The results are shown in Table 3. As shown in Table 3, Compounds 1 and 2 showed a significant radioactive accumulation like $^{123}$I-IMPY at the time point of two minutes after the injection, and then showed a tendency to rapidly clear away in 60 minutes. These results suggest that both Compounds 1 and 2 possess excellent transferability to brain and rapid clearance from brain like $^{123}$I-IMPY.

TABLE 3

Radioactive accumulation in brain of the present compound after intravenous injection (rats)

Radioactive accumulation per unit weight (% ID/g)

| Compound | After 2 min. | After 5 min. | After 15 min. | After 30 min. | After 60 min. |
|---|---|---|---|---|---|
| Compound 1 | 1.085 | 0.701 | 0.260 | 0.100 | 0.034 |
| Compound 2 | 1.201 | 1.065 | 0.745 | 0.349 | 0.113 |
| [$^{123}$I]-IMPY | 1.644 | 1.192 | 0.554 | 0.225 | 0.085 |

Example 8

Confirmation of Compound Avidity for Brain Slice of AD Patients by Autoradiography The following experiment was carried out in order to examine whether amyloid in brain of AD patients can be imaged by the compound of the present invention.

Method (1) A 5 μm-thick brain slice of AD patients was prepared from a brain tissue of AD patients available from Analytical Biological Services Inc. (United States).

(2) The brain slice was immersed in PBS for 15 minutes, 5 minutes and 5 minutes each. Next, it was immersed in a 1% BSA-containing PBS for 30 minutes, and then a 1% BSA-containing PBS containing each of Compound 1, Compound 2 and [$^{123}$I]-IMPY (radioactive concentration: 10 kBq/mL) was prepared, and the brain slice was immersed therein under room temperature for 30 minutes. Then, it was immersed in a 1% BSA-containing PBS solution, a PBS solution and a PBS solution each for 5 minutes to wash the brain slice. The washed brain slice was sufficiently dried, and then exposed to an imaging plate for 16 hours, and then autoradiogram image analysis was carried out by use of a Bio-imaging Analyzer (type: BAS-2500; manufactured by FUJIFILM Corporation) (FIG. 3, FIG. 4, FIG. 5).

Figure 6:
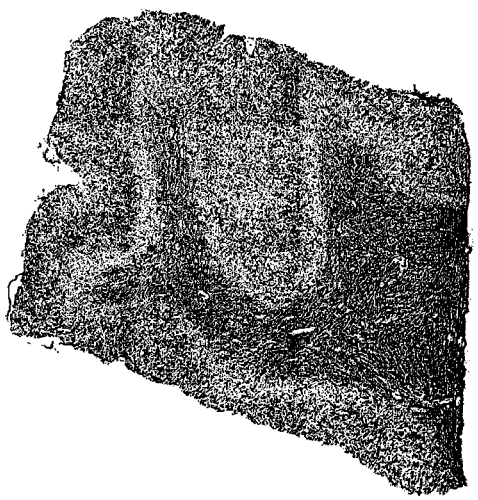
FIG. 6 is an immunostaining of a brain slice of an AD patient using anti-amyloid antibody.

(3) Immunostaining at a site of amyloid deposition with an anti-amyloid antibody was carried out using adjacent slices. Anti-Human Amyloidβ (N) (82E1) Mouse IgG MoAb (Immuno-Biological Laboratories Co., Ltd.) was used as the anti-amyloid antibody, and Anti-Mouse IgG (H+L) Goat IgG Fab'-HRP (Immuno-Biological Laboratories Co., Ltd.) was used as a secondary antibody. The site of amyloid deposition was detected by applying the DAB+ (3,3'-diaminobenzidinetetrahydrochloride).substrate kit (Dako) to HRP attached to the secondary antibody (FIG. 6).

Results

Figure 3:
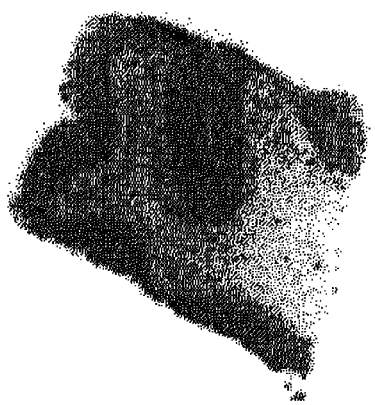
FIG. 3 is an autoradiography of a brain slice of an AD patient using [$^{123}$I]-6-iodo-2-[4-(1H-1,2,3,-triazole-1-yl)phenyl]imidazo[1,2-a]pyridine.
Figure 4:
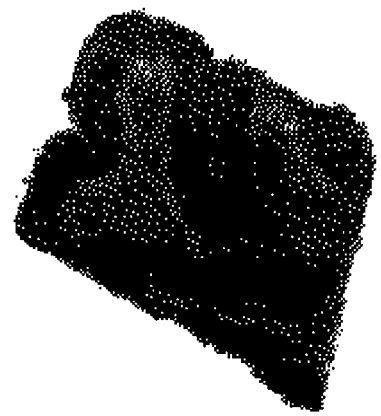
FIG. 4 is an autoradiography of a brain slice of an AD patient using [$^{123}$I]-6-iodo-2-[4-(1H-pyrrole-1-yl)phenyl] imidazo[1,2-a]pyridine.
Figure 5:
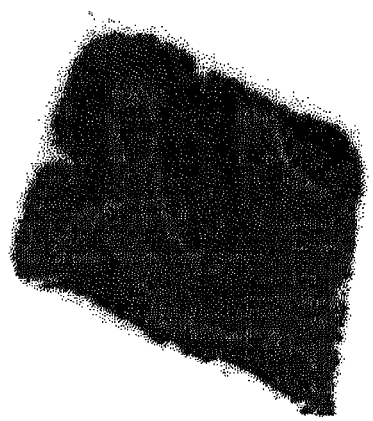
FIG. 5 is an autoradiography of a brain slice of an AD patient using [$^{123}$I]-IMPY.

FIG. 3, FIG. 4 and FIG. 5 show autoradiograms of the slice immersed in the solution containing Compound 1, Compound 2 and [$^{123}$I]-IMPY, respectively. Amyloid deposition was confirmed by immunostaining at a gray matter site of frozen brain slice of AD patients used in this experiment (FIG. 6), and the binding of the compounds to the site of amyloid deposition confirmed by immunostaining was also be confirmed on the respective autoradiograms.

These results suggest that Compound 1 and Compound 2 according to the present invention can image the site of amyloid deposition in the brain like [$^{123}$I]-IMPY.

INDUSTRIAL APPLICABILITY

The compounds of the present invention can be utilized in the field of diagnostic agents.

The invention claimed is:

1. A compound represented by the following formula (1), or a salt thereof:

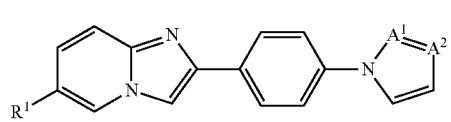

(1)

wherein $R^1$ is a radioactive halogen substituent, and $A^1$ and $A^2$ independently represent CH or N.

2. A compound or a salt thereof according to claim 1, wherein $R^1$ is selected from the group consisting of $^{18}$F, $^{76}$Br, $^{123}$I, $^{124}$I, $^{125}$I and $^{131}$I.

3. A compound represented by the following formula (2), or a salt thereof:

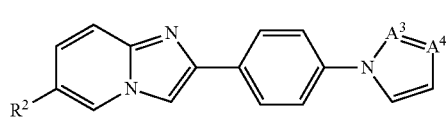

(2)

wherein $R^2$ is a group selected from the group consisting of a non-radioactive halogen substituent, nitro group, trialkylammonium group having alkyl chains with 1 to 4 carbon atoms, trialkylstannyl substituent having alkyl chains with 1 to 4 carbon atoms and triphenylstannyl group, and $A^3$ and $A^4$ independently represent CH or N.

4. A diagnostic agent for Alzheimer's disease, which comprises a compound represented by the following formula (1), or a salt thereof:

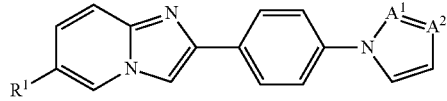

(1)

wherein $R^1$ is a radioactive halogen substituent, and $A^1$ and $A^2$ independently represent CH or N.

5. The diagnostic agent for Alzheimer's disease according to claim 4, wherein $R^1$ is a radioactive halogen substituent selected from the group consisting of $^{18}$F, $^{76}$Br, $^{123}$I, $^{124}$I, $^{125}$I and $^{131}$I.

* * * * *